(12) United States Patent
Pickhard et al.

(10) Patent No.: US 9,289,563 B2
(45) Date of Patent: Mar. 22, 2016

(54) SYRINGE WITH SYRINGE BARREL, SYRINGE HEAD AND EJECTOR UNIT

(75) Inventors: Ewald Pickhard, Grossebersdorf (AT); Andreas Schwirtz, Vienna (AT)

(73) Assignee: Pharma Consult Ges.m.b.H., Vienna (AT)

( * ) Notice: Subject to any disclaimer, the term of this patent is extended or adjusted under 35 U.S.C. 154(b) by 310 days.

(21) Appl. No.: 14/000,927

(22) PCT Filed: Feb. 23, 2012

(86) PCT No.: PCT/AT2012/050024
§ 371 (c)(1),
(2), (4) Date: Oct. 17, 2013

(87) PCT Pub. No.: WO2012/113008
PCT Pub. Date: Aug. 30, 2012

(65) Prior Publication Data
US 2014/0052071 A1  Feb. 20, 2014

(30) Foreign Application Priority Data

Feb. 23, 2011 (AT) .................................. GM107/2011
May 12, 2011 (AT) ................................... A 680/2011

(51) Int. Cl.
| A61M 5/34 | (2006.01) |
| A61M 5/28 | (2006.01) |
| A61M 5/24 | (2006.01) |
| A61M 5/32 | (2006.01) |
| A61M 5/50 | (2006.01) |
| A61M 5/31 | (2006.01) |

(52) U.S. Cl.
CPC ............. *A61M 5/347* (2013.01); *A61M 5/2466* (2013.01); *A61M 5/288* (2013.01); *A61M 5/322* (2013.01); *A61M 5/3234* (2013.01); *A61M 5/3202* (2013.01); *A61M 5/345* (2013.01); *A61M 5/502* (2013.01); *A61M 5/508* (2013.01); *A61M 2005/2474* (2013.01); *A61M 2005/312* (2013.01); *A61M 2005/3139* (2013.01); *A61M 2005/3235* (2013.01); *A61M 2005/3238* (2013.01)

(58) Field of Classification Search
CPC . A61M 5/2466; A61M 5/288; A61M 5/3203; A61M 5/322; A61M 5/3234; A61M 5/344; A61M 5/345; A61M 5/347; A61M 5/502; A61M 5/508; A61M 2005/2433; A61M 2005/2444; A61M 2005/2474; A61M 2005/312; A61M 2005/3139; A61M 2005/3235; A61M 2005/3238
USPC .......... 604/187, 192, 193, 199, 200, 201, 206
See application file for complete search history.

(56) References Cited

U.S. PATENT DOCUMENTS

| 5,250,037 A | 10/1993 | Bitdinger |
| 6,053,892 A | 4/2000 | Meyer |
| 6,613,016 B1 | 9/2003 | Ku |
| 2002/0111588 A1 | 8/2002 | Restelli |
| 2009/0312703 A1 | 12/2009 | Pickhard |
| 2011/0046561 A1 | 2/2011 | Pickhard |

FOREIGN PATENT DOCUMENTS

| AT | 404 430 B | 11/1998 |
| AT | 505 616 A4 | 3/2009 |
| DE | 693 19 702 T2 | 2/1999 |
| EP | 1 232 763 A1 | 8/2002 |
| WO | WO 03/057289 A1 | 7/2003 |
| WO | WO 2007/112470 A1 | 10/2007 |
| WO | WO 2009/097634 A1 | 8/2009 |

OTHER PUBLICATIONS

International Search Report of PCT/AT2012/050024, date of mailing Jul. 20, 2012.
International Preliminary Report on Patentability of PCT/AT2012/050024, Aug. 23, 2013.

*Primary Examiner* — Edelmira Bosques
*Assistant Examiner* — Nicholas Meghri
(74) *Attorney, Agent, or Firm* — Collard & Roe, P.C.

(57) ABSTRACT

The invention relates to a syringe (20) comprising a syringe barrel (15), an ejector unit (25) arranged at the distal end of the syringe barrel (15) with a plunger rod (17), a coupling part (37) and a plunger (16) and a syringe head (21) arranged at the proximal end of the syringe barrel (15) with a needle unit (12) which is arranged in a guide sleeve (5) and is slidable therein with a cannula (3) and a cannula holder (4) and a pinion (2), by means of which the needle unit (12) is axially movable, relative to a syringe barrel (15) from a rest position to an actuation position. At the distal end of the guide sleeve (5) a sealing element (7) is arranged. The pinion (2) has at least one guide knob (1), which can be brought into engagement optionally with one of two slide tracks (10) provided in the guide sleeve (5), wherein the slide tracks (10) are inclined in opposite directions.

20 Claims, 10 Drawing Sheets

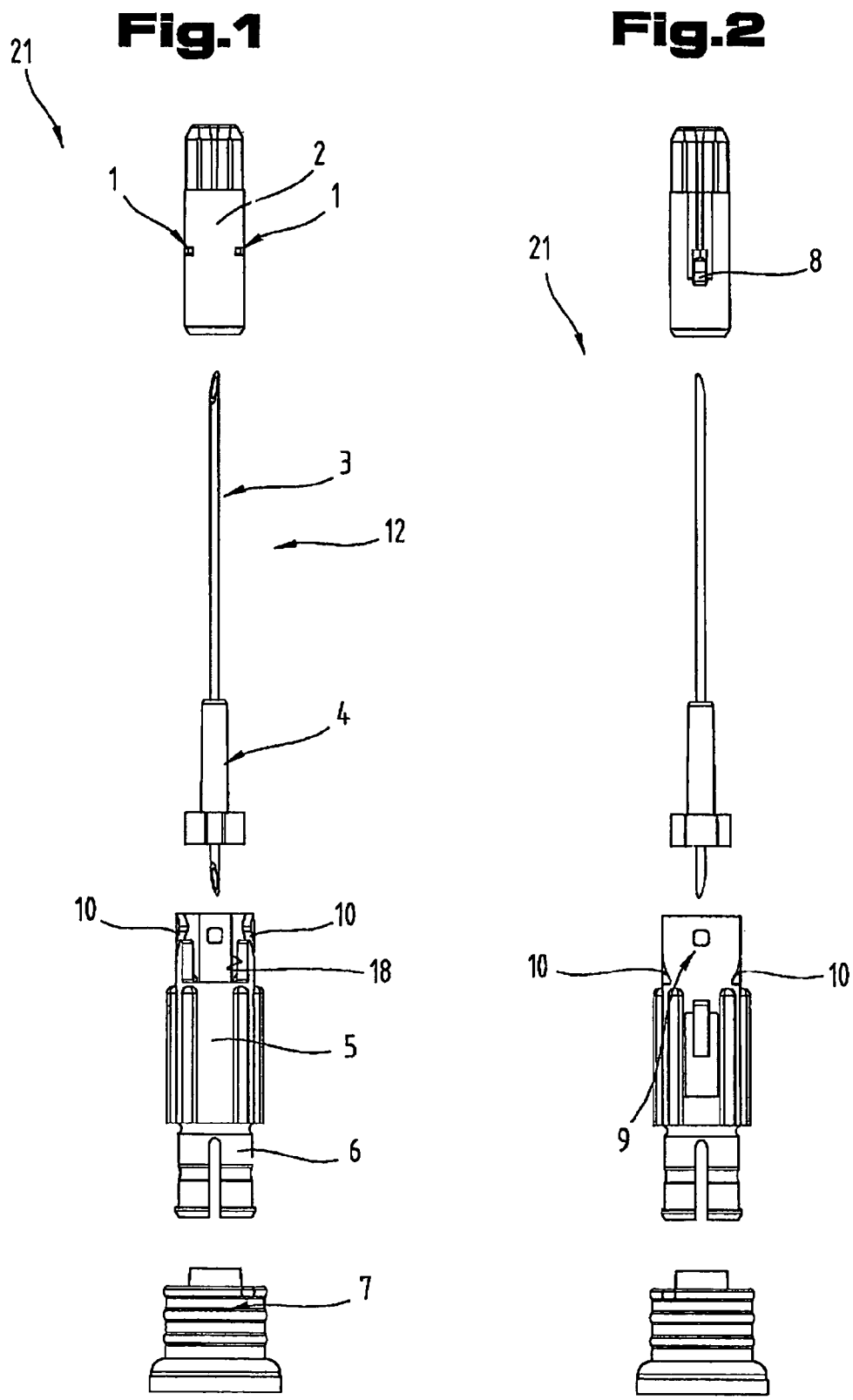

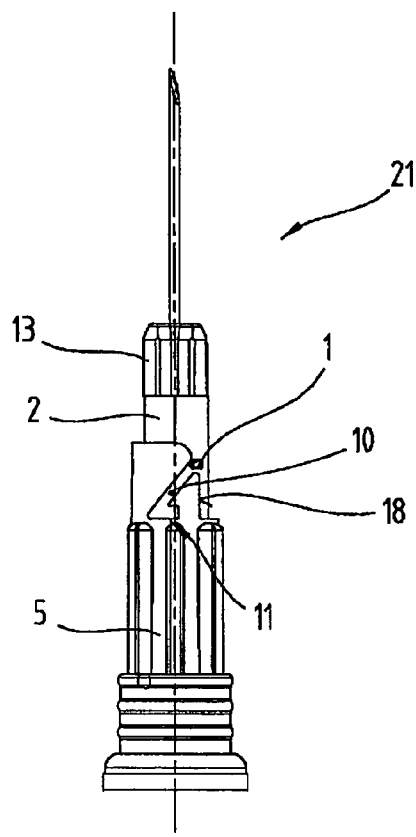
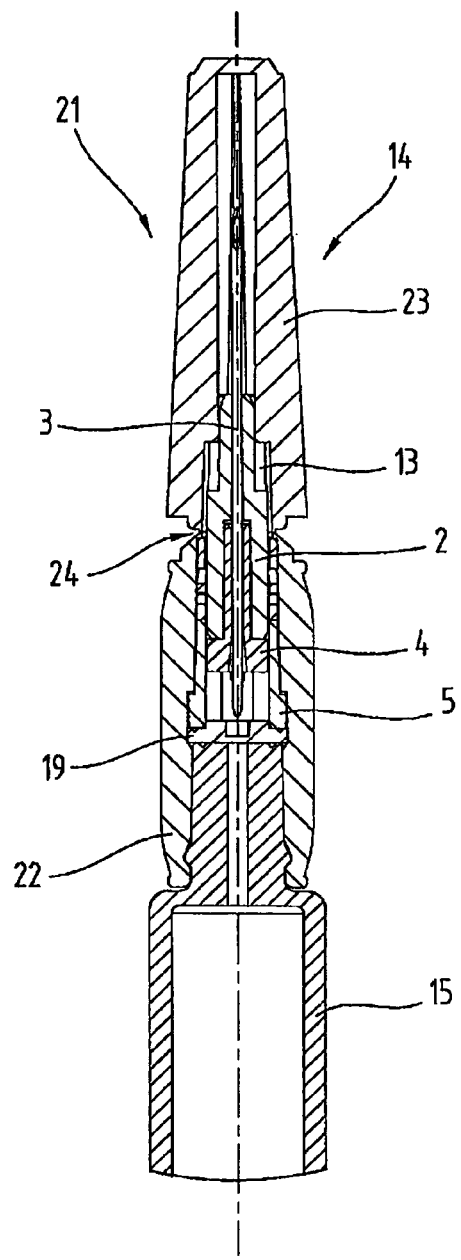

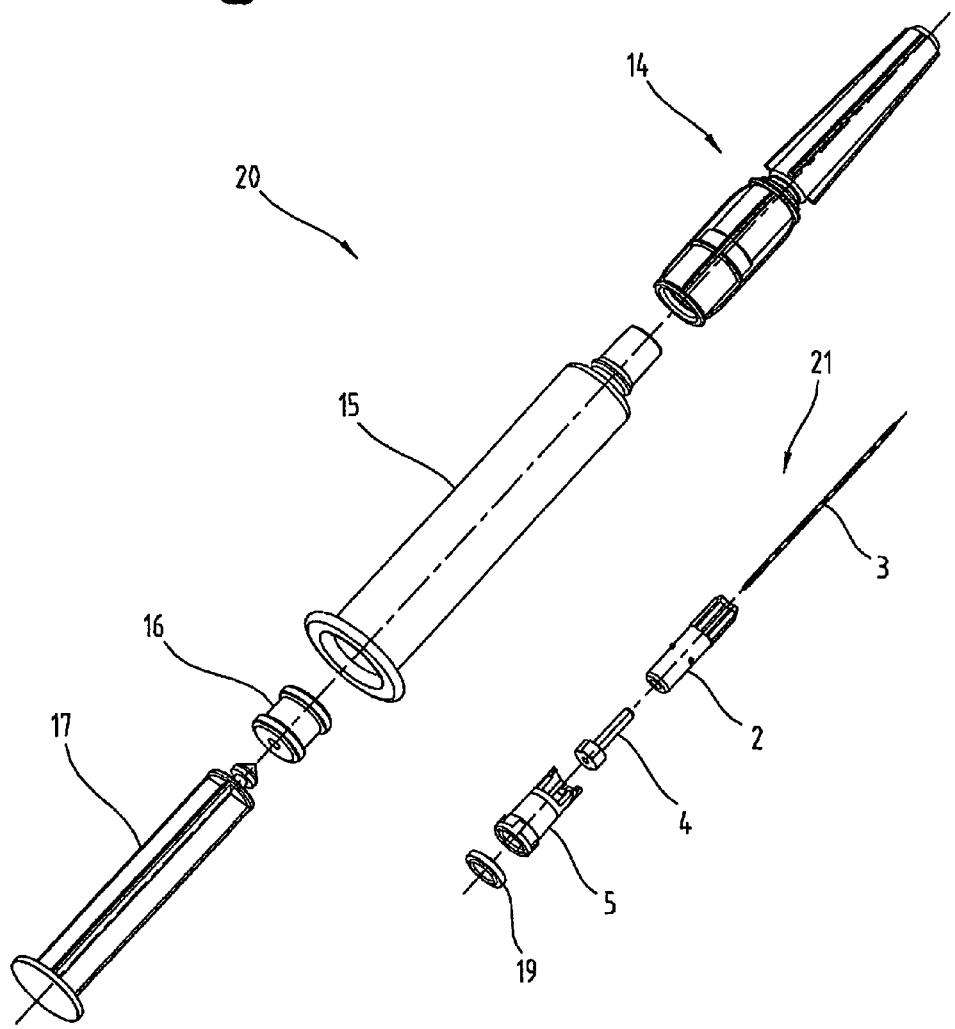

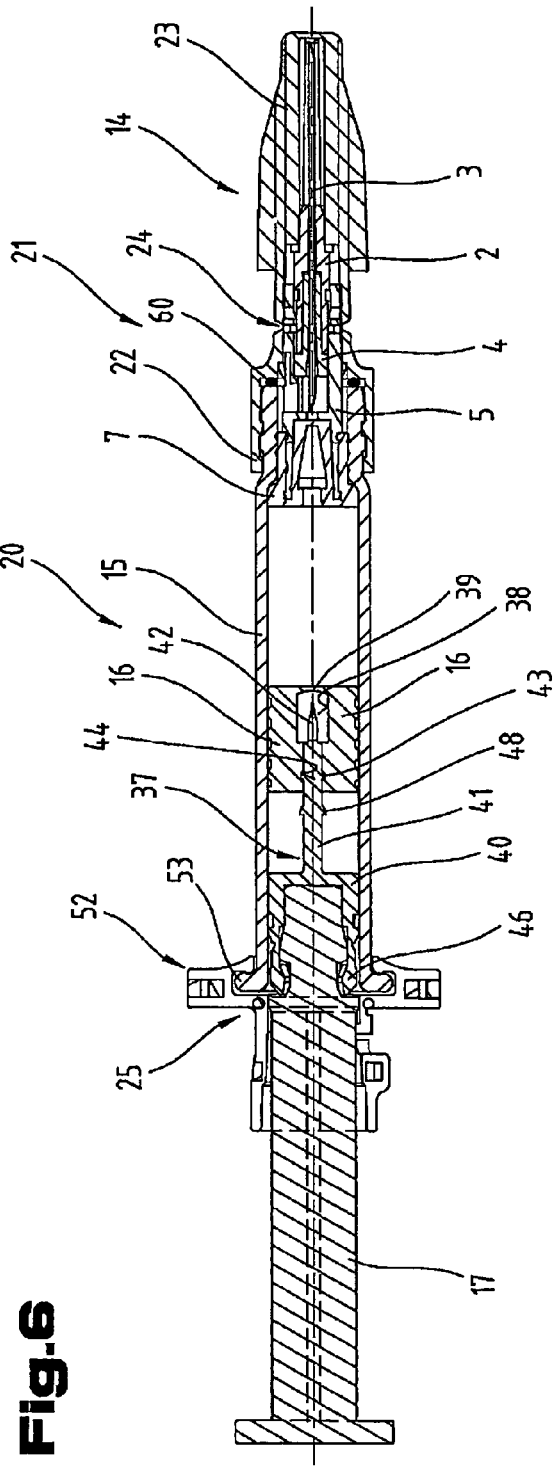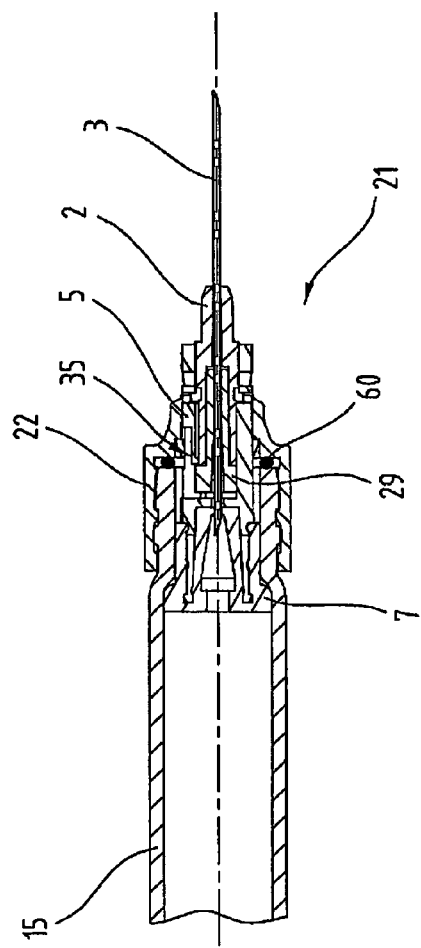

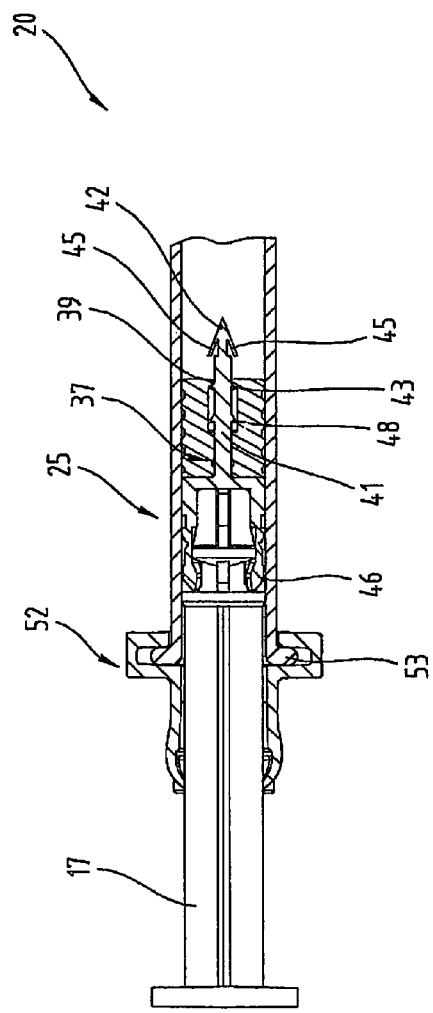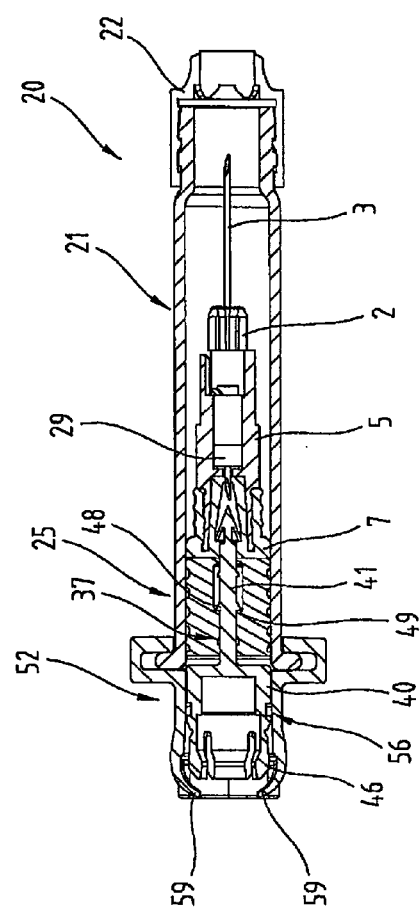

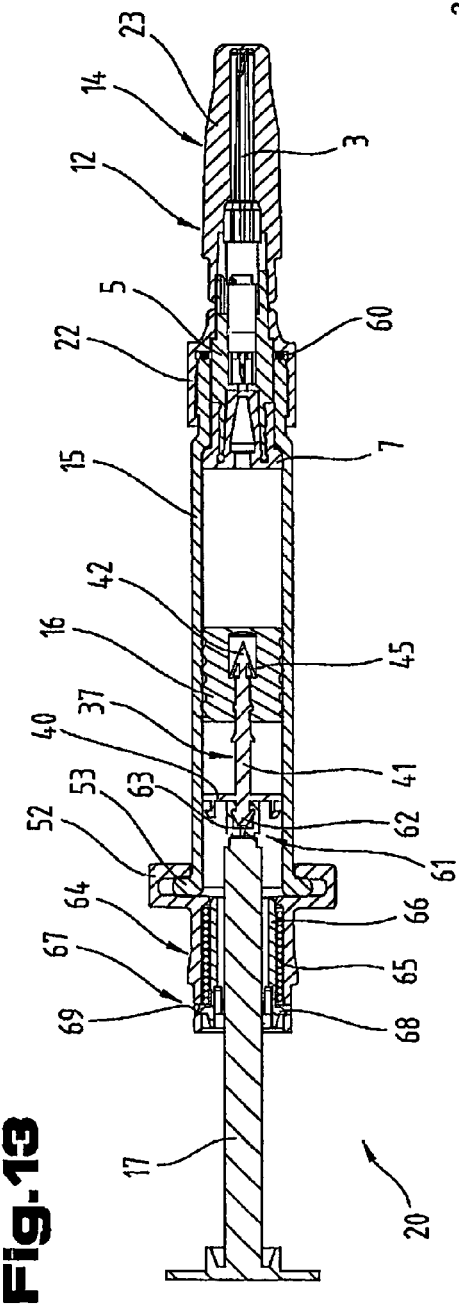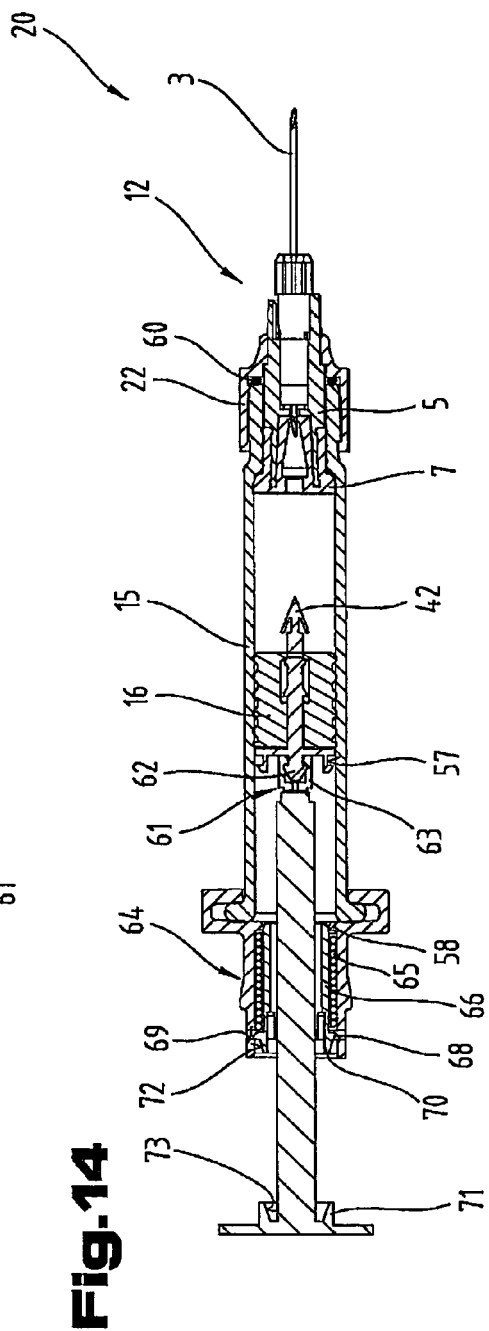

SYRINGE WITH SYRINGE BARREL, SYRINGE HEAD AND EJECTOR UNIT

CROSS REFERENCE TO RELATED APPLICATIONS

This application is the National Stage of PCT/AT2012/050024 filed on Feb. 23, 2012, which claims priority under 35 U.S.C. §119 of Austrian Application Nos. GM 107/2011 filed on Feb. 23, 2011, and A 680/2011 filed on May 12, 2011, the disclosures of which are incorporated by reference. The international application under PCT article 21(2) was not published in English.

The invention relates to a syringe comprising a syringe barrel for holding a medicine to be administered, an ejector unit arranged at the distal end of the syringe barrel, a syringe head arranged at the proximal end of the syringe barrel with a needle unit arranged in a guide sleeve and slidable therein with a cannula and a cannula holder and a pinion, by means of which the needle unit can be moved axially relative to a syringe barrel from a position of rest to an actuation position and a sealing element arranged at the distal end of the guide sleeve, which in the position of rest of the needle unit is unpierced by the cannula and in the activation position of the needle unit is pierced by the cannula.

In the present description the directions "proximal" and "distal" are defined from the side of the patient. Thus the proximal side of the components described in the following is always turned towards the patient and the distal side is always turned away from the patient. Syringes, in particular disposable syringes, are known for the administration of medicine. In the case of disposable syringes, which are often used by patients themselves, the cannula is only connected to the syringe barrel just before use by a rotational movement.

From AT 404 430 B a syringe head is known, in which the cannula pierces a sealing disc at the outlet of the syringe barrel by means of either a left or right-hand rotation, so that the patient does not need to be given any instructions in advance about which direction to turn it or be told whether one direction of rotation would prevent the safe use of the syringe. For this according to the teaching of AT 404 430 B a cannula support is inserted into a cannula support guide, wherein the cannula support comprises a Y-shaped guide groove branching towards the proximal end, into which groove a guide pin engages in the cannula support guide. On rotating the cannula support the guide pin runs either through the left or the right side of the groove, whereby the cannula support moves in a right or left rotation in the direction of the sealing disc. The disadvantage of this solution is that the guide pin has to be arranged on the inside of the cannula support guide, which is expensive to manufacture and is associated with high reject rates. A further disadvantage is that it is also possible for the cannula support to be guided out of the end position and the user is able disconnect the connection between the cannula and pierced sealing disc either intentionally and unintentionally. Furthermore, it is a disadvantage that the sharpened distal end of the cannula is rotated into the sealing disc and during the piercing may cause the formation of abrasion particles from the material of the sealing disc which then might get into the liquid medicine. Furthermore, the used cannula can only be protected after use by refitting a part of the protective cap, which may cause needlestick injuries.

From U.S. Pat. No. 5,250,037 A and/or DE 693 19 702 T2 a syringe head of the aforementioned kind is known in which a pinion connects a needle unit to the syringe barrel prior to injection. The disadvantage here is that the pinion is at the same time the protective cap of the syringe and after activation is removed therefrom. Consequently, the needle unit is only connected loosely and unsecurely to the syringe barrel during the injection process. Here too the used cannula can only be protected after use by refitting the protective cap, which may cause needlestick injuries.

Another syringe is known from WO 2009/097634 A1. In this case this syringe comprises a syringe head covered by a protective cap in the starting position, which syringe head comprises a cannula held in a cannula holder, a guide sleeve mounting the cannula holder and the cannula and a drive element for adjusting the cannula together with the cannula holder. At the end facing the syringe barrel a sealing insert is snapped onto the guide sleeve. To convert the rotational movement from the protective cap tip to the drive part and then to the cannula holder the drive part is provided on its outside with a slide track which cooperates with a guide pin on the inside of the guide sleeve. Here too the disadvantage is that the guide pin is arranged on the inside of the guide sleeve, which is expensive to manufacture and is associated with high reject rates. At the same time however there is also no clear end position for the cannula with its cannula holder in the activated position, in which the cannula penetrates the bottom of the sealing insert. Furthermore, there may be an unintentional displacement of the coupling part relative to the plunger which means that the seal and most of all the sterility are no longer guaranteed.

From US 6,613,016 B1 a syringe is known with a syringe barrel for holding a medicine to be administered, in which at the distal end of the syringe an ejector unit is arranged and at the proximal end thereof a syringe head is arranged. The syringe head comprises a holding element mounted displaceably in the syringe barrel for a needle arrangement insertable therein. In this case the needle arrangement is constantly in flow connection with the inner chamber of the syringe barrel. The ejector unit comprises a plunger rod with a rod-like element connected securely thereto, which on the side facing the inner chamber of the syringe has an arrow-tip-shaped or wedge-shaped end. On this rod-like plunger rod body a tubular adapter is mounted displaceably, which in a starting position is held locked by a locking or retaining device relative to the rod-like plunger rod body. At its end facing the syringe barrel the elastically deformable plunger is held or arranged. After the complete ejection of the medicine to be delivered the locking device disengages between the tubular adapter and the rod-like plunger rod body and the arrow-like end of the plunger rod body pierces the sealing plug and continues to penetrate into the holding element of the syringe head. In this way a coupling process is performed by means of which the entire syringe head can be pulled back into the inner chamber of the syringe barrel.

The present invention aims to create a syringe with a syringe head and an ejector unit of the aforementioned kind which avoids these disadvantages, and in particular after connecting the cannula to the syringe barrel prevents the further movement of the cannula. A further aim of the invention is to connect the cannula to the syringe barrel so that no abrasion particles can be produced. Furthermore, also an improved coupling connection is created between the plunger and the coupling part of the ejector unit.

The syringe head according to the invention achieves this in that the pinion comprises at least one guide knob, which can be moved optionally into engagement with one of two slide tracks provided in the guide sleeve, wherein the slide tracks are inclined in opposite directions.

It is advantageous in this case that the guide knob can be configured more easily by molding and most of all that the safety of the function of the whole syringe can be increased. Furthermore, the configuration of the slide tracks can also be simpler and most of all safer to use. In this way a compact and most of all safe and easy to use syringe is created which can be used by non-medically trained persons and also has a high degree of operating safety.

According to a further configuration the pinion comprises two guide knobs which are arranged spaced apart from one another in a plane perpendicular to a longitudinal axis and in circumferential direction and for the displacement of the needle unit from the position of rest to the actuation position only one of the two guide knobs can be moved into engagement with one of the two slide tracks. In this way the operating safety is increased further and the facility of the operation is improved.

A further preferred embodiment has the features that in the guide sleeve in a circumferential area between the two slide tracks a free space is formed and the free space is used for mounting the guide knob which during the adjustment of the needle unit is not in engagement with any of the slide tracks. In this way despite the two guide knobs on the one hand there can be an exact guiding of one of the two knobs and on the other hand jamming is prevented during the rotational movement.

Another embodiment is characterized in that the needle unit, in particular its cannula holder, and the guide sleeve are held in the actuation position in axial direction relative to one another by means of interacting locking elements of a locking device. In this way before, during and after the administration of the medicine a secured position of the cannula can always be achieved and unwanted axial displacement is avoided.

According to a further embodiment the needle unit, in particular its cannula holder, is coupled to the pinion about the longitudinal axis but locked in axial direction. In this way there can be preassembly of the cannula holder and cannula in the pinion, without the necessary freedom of movement of rotatability being restricted.

A further preferred embodiment has the features that the needle unit, in particular its cannula holder, is mounted guided linearly in axial direction in the guide sleeve. In this way a clean piercing movement is performed in the region of the sealing element and the separation of particles of the sealing element is avoided. In this way an even safer delivery of the medicine is achieved with regard to its purity.

A further embodiment is characterized in that at the end of each slide track a slide extension is provided, into which the guide knob can be locked. By having an additional locking hook the latter can also be configured to lock into the slide extension.

A further preferred embodiment is characterized in that the distal end of the guide sleeve is in the form of a coupling. Alternatively the distal end of the guide sleeve can be configured to be flat.

According to a further configuration on an outer side of the guide sleeve at least one longitudinal rib is arranged, which is supported to be non-rotational on a locking element of a protective cap mounting the syringe head. In this way the rotation of the guide sleeve is prevented during the activation process.

A further preferred embodiment is characterized in that the ejector unit comprises a plunger rod, a coupling part with a base body and a coupling extension extending to the side facing away from the plunger rod and a plunger, wherein the base body of the coupling part is coupled detachably to the plunger rod and the plunger has a blind hole extending from an end facing towards the plunger rod, which hole is closed by a bottom, wherein the coupling extension of the coupling part projects into the blind hole and is arranged in an inactivated starting position of the plunger in axial direction spaced apart from the base body and also the bottom of the blind hole is not pierced by a coupling extension end of the coupling extension, wherein on the coupling extension at least one first locking element is arranged, which in the inactivated starting position is inserted into a locking recess arranged in the plunger in the area of the blind hole. The advantages resulting therefrom are that in this way a preassembly and most of all a secure insertion of the plunger into the syringe barrel can be performed. This mount acting in axial direction can be overcome for ejecting the medicine and is also used during transport and storage so that the plunger remains undamaged in the region of its blind hole. In this way unwanted displacement is also avoided in the case of vibrations.

A further embodiment is characterized in that the first locking element in a position of the base body and the plunger lying against one another bears on the bottom of the blind hole in the area passed through by the coupling extension. In this way a supporting effect of the pierced bottom is achieved and the seal tightness is ensured in this section even during the ejection of the medicine.

According to a further configuration an additional locking element is arranged on the coupling extension between the base body and the first locking element, which locking element bears against a shoulder formed in the blind hole of the plunger during the restoring moment of the ejector unit. In this way the restoring movement is made easier and stiffening of the carried along syringe head is also prevented.

A further embodiment is characterized in that the coupling extension end is configured to taper arrow-like to the side facing away from the plunger rod and comprises at least one, preferably two locking arms projecting over the cross section of the coupling extension. In this way for the coupling movement the penetration force is reduced and also the retaining force is increased by the formation of a more stable shoulder in the sealing element. Furthermore, in this way particularly with a sealing element coated in lubricant a better anchoring effect or hooking of the locking arm or arms can be achieved by partial penetration into the elastic material of the sealing element.

According to a further embodiment the base body of the coupling part comprises elastically deformable coupling arms on the side facing the plunger rod, which are coupled detachably to a coupling element formed on the plunger rod. In this way the disconnection of the plunger rod can be performed easily after the restoring movement of the entire needle unit.

A further preferred embodiment is characterized in that the ejector unit also comprises an handling element, which can be coupled to a distal end of a syringe barrel, and an internal inner width of a through channel in the handling element at a distal section is configured to be larger than an external cross-sectional dimension of the coupling arms in their undeformed position. In this way the syringe barrel can be configured simply with an almost identical internal dimension over the largest part of its structural length. In this way molding costs and inaccurracies in the production of the syringe barrel are avoided. By means of the additionally connectable handling element the operating safety can be increased and most of all re-use can be prevented by having simpler components.

A further embodiment is characterized in that between the base body of the coupling part and the handling element a holding device is formed with interacting holding elements, which when the holding elements are in engagement prevent at least an axial displacement of the coupling part in proximal direction. In this way mainly it is possible to prevent unintentional re-use and in this connection the possible transmission of diseases.

According to a further embodiment at least one guiding element is arranged on the handling element in the region of its distal end, which guiding element projects into the cross section of the through channel. In this way after disconnecting the plunger rod from the coupling part with the protected needle unit its re-insertion and re-use are prevented.

Another embodiment is characterized in that between the handling element and the plunger rod a resetting device is provided, by means of which the plunger rod, the coupling part, the plunger and the possibly connectable needle unit can be reset in distal direction relative to the syringe barrel. In this way after the release or triggering of the resetting device an automatic safety position of the used cannula inside the syringe barrel can be achieved.

According to a further configuration the resetting device comprises at least one spring element, which at its proximal end is supported on the handling element and at its distal end is supported on a tubular sliding body, and the sliding body in the pretensioned position of the spring element is held on the handling element by means of a retaining device, if necessary detachably. Thus the established or stored resetting energy can be maintained during the administration process and the movement of the plunger rod for the administration process can be performed without hindrance.

A further preferred embodiment has the features that the release of the retaining device is performed according to a predefined adjustment movement of the plunger rod relative to the syringe barrel by means of interacting adjusting elements, wherein at least one first adjusting element is arranged on the sliding body and at least one further adjusting element is arranged on the plunger rod. In this way without the additional intervention of the user of the syringe the resetting device can be triggered automatically. In this way a so-called passive needle withdrawal can be achieved, in particular of the cannula, into the syringe barrel. In this way depending on the predetermined or predefined adjustment movement, which is absolutely necessary to bring the adjusting elements into engagement with one another, on the one hand the minimum administration amount of the medicine can be determined and on the other hand the user can be freed from making an absolutely necessary triggering movement for the resetting of the cannula into its safety position.

Another embodiment is characterized in that the material of the syringe is selected to be glass and the inner chamber of the syringe is filled with medicine and is ready to be administered, wherein the inner chamber holding the medicine is sealed completely so as to be bacteria-proof against the inner wall of the syringe barrel at its proximal end by the sealing element which is unpierced until activated and at its distal end by the plunger that is also not yet pierced. Thus this is a type of syringe in which the medicine is already prefilled and is ready to be administered. This is referred to as a prefilled syringe, in particular a glass single-dose syringe. Only after the activation of the syringe head by rotating the protective cap tip does the distal end of the cannula pierce the base of the sealing element and thus creates the line connection to the inner chamber of the syringe barrel and thereby the medicine. The stored medicine can then be administered.

The invention is explained in more detail in the following with reference to the exemplary embodiments shown in the drawings.

In a much simplified representation:

FIG. 1 shows an exploded view of the syringe head;

FIG. 2 shows an exploded view of the syringe head rotated axially by 180°;

FIG. 3 shows a syringe head rotated axially by 90°;

FIG. 4 shows an exploded view of a syringe in an alternative embodiment;

FIG. 5 shows a cross section of the syringe head of an alternative embodiment;

FIG. 6 shows a further possible configuration of a syringe in an unopened original position, in cross-sectional view;

FIG. 7 shows the syringe head of the syringe after the activation of the syringe according to FIG. 6, in cross-sectional view;

FIG. 8 shows the ejector unit of the syringe after the activation of the syringe according to FIG. 6, in cross-sectional view;

FIG. 9 shows the disposal position of the syringe according to FIGS. 6 to 8, in cross-sectional view;

FIG. 13 shows a further and possibly independent configuration of a syringe with an automated passive resetting device for the needle unit in the starting position, in cross-sectional view;

FIG. 14 shows the syringe according to FIG. 13, during the delivery of the medicine, in cross-sectional view;

FIG. 15 shows the syringe according to FIGS. 13 and 14, during the release of the resetting device, in cross-sectional view;

FIG. 16 shows the syringe according to FIGS. 13 to 15, in the protected position of the needle unit inside the syringe barrel, in cross-sectional view.

Figure 10:
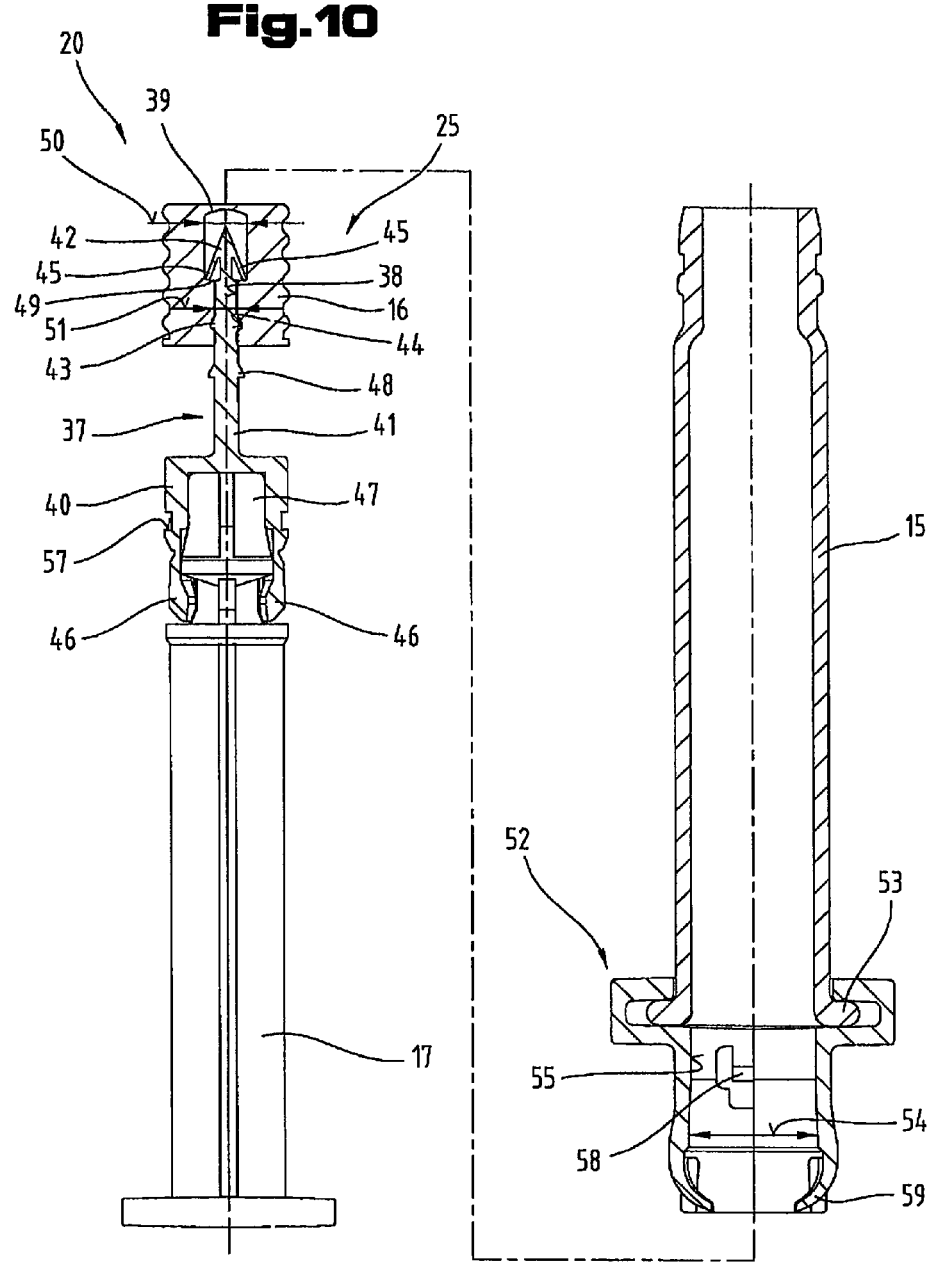
FIG. 10 shows the ejector unit and the syringe barrel with handling element according to FIGS. 6 to 9 in an exploded view, in cross-sectional view.

First of all, it should be noted that in the variously described exemplary embodiments the same parts have been given the same reference numerals and the same component names, whereby the disclosures contained throughout the entire description can be applied to the same parts with the same reference numerals and same component names. Also details relating to position used in the description, such as e.g. top, bottom, side etc. relate to the currently described and represented figure and in case of a change in position should be adjusted to the new position.

A syringe head 21 according to FIG. 1 comprises a needle unit 12 with a cannula 3 and a cannula holder 4. The needle unit 12 is inserted into a guide sleeve 5. The drive of the needle unit 12 in the direction of a not shown syringe barrel, for connecting the cannula 3 to the sealed syringe barrel directly prior to the injection, is performed by a pinion 2, which is fitted onto the needle unit 12. The pinion 2, the cannula holder 4 and the guide sleeve 5 are preferably made of plastic.

FIG. 3 shows the finally connected syringe head 21. The pinion 2 comprises two guide knobs 1, which are arranged respectively in the inactivated state of the syringe head 21 before the entry of a slide track 10. The slide tracks 10 are recesses in the guide sleeve 5. They run on the guide sleeve 5 and are inclined in opposite directions. If the pinion 2 is rotated, which can mean for example that lamellae of a protective cap not shown in FIGS. 1 to 3 engage in webs 13 of the pinion 2 running on a longitudinal axis 19, one of the guide knobs 1 is guided into one of the slide tracks 10, whereas the other guide knob 1 enters unhindered into a free space or a free position 18 of the guide sleeve 5. The guide knob 1, which is guided in a slide track 10 follows the inclination of this slide track 10 and moves the pinion 2 together with the needle unit 12 in the direction of the syringe barrel. In this way the needle unit 12 is moved towards the syringe barrel by both a left rotation and a right rotation. The size of the needle unit 12 and the correspondingly shaped inner channel of the guide sleeve 5 are configured so that the needle unit 12 cannot perform a rotation when driven by the pinion 2 but is moved linearly in the direction of the syringe barrel. According to FIGS. 1 to 3 the rotation of the pinion 2 for the complete movement of the needle unit 12 is about 90°.

The pinion 2 according to FIG. 2 also comprises a locking hook 8 which is arranged approximately at the level of the guide knobs 1 on the other circumferential side of the pinion 2. In the inactivated state of the syringe head 21 the locking hook 8 is positioned in a window 9 of the guide sleeve 5. In order to move the locking hook 8 out of this position it is necessary to overcome a mechanical resistance, whereby the syringe head 21 is secured in its inactivated state from unintentional activation. During the rotation of the pinion 2 the locking hook 8 moves up to the end of the slide track 10, which is not occupied by a guide knob 1. The slide tracks 10 each comprise a horizontal slide extension 11 according to FIG. 3. After executing the pinion rotation in one slide extension 11 there is a guide knob 1 and in the other slide extension 11 there is the locking hook 8. The removal by rotation of the pinion 2 and thereby a further movement of the needle unit 12 is now no longer possible, as the opposite inclinations of the slide tracks 10 mutually lock the movements of the guide knob 1 and the locking hook 8. This favors the safe handling of the syringe, as the repeated connection and disconnection of the cannula from the syringe barrel is not possible.

The syringe head 21 comprises in a first embodiment according to FIGS. 1 to 3 at its distal end a coupling 6, which is preferably configured as a distal end of the guide sleeve 5. The coupling 6 can be connected for example to a sealing element 7 of the syringe barrel in the form of a plug-in connection. The distal end of the sealing element 7 can be connected securely to the syringe barrel or be part of a component group insertable into the syringe barrel after the injection. In this way the syringe head 21 can be fitted onto a plurality of syringe types.

FIG. 4 shows a complete syringe 20 according to the invention in a second embodiment form. The distal end of the guide sleeve 5 is configured to be flat and connects to a sealing disc 19. In the assembled state the sealing disc 19 lies on the proximal end of a syringe barrel 15 into which a plunger rod 17 and a plunger 16 are inserted for moving the fluid. The syringe head of the syringe barrel 15 together with the syringe head 21 are covered by a protective cap 14.

According to FIG. 5 the protective cap 14 is fitted onto the syringe barrel 15 and thereby presses the guide sleeve 5 onto the sealing disc 19 and the proximal end of the syringe barrel 15. The protective cap 14 comprises in a known manner a protective cap base 22 and a protective cap tip 23, which are connected by means of a predetermined breaking point 24. By rotating the protective cap tip 23 the predetermined breaking point 24 between the latter and the protective cap base 23 is broken. Inner lamellae of the protective cap tip 23 engage with the webs 13 of the pinion 2 and thereby also set it into rotation. Thus lastly the pinion 2 and the needle unit 12 are moved in the aforementioned manner in the direction of the syringe barrel 15 and the sealing disc 19 is pierced.

Independently of this it would also be possible to have only a single guide knob 1 on the pinion 2 and to move said guide knob 1 optionally into engagement with one of the two opposite slide tracks 10 according to the chosen direction of rotation (clockwise or counterclockwise) and thus bring about the associated adjustment of the cannula holder 4 with the cannula 3 in the direction of the syringe barrel 15. Furthermore, the arrangement or provision of the locking hook 8 in connection with the window 9 can be completely dispensed with, which means that simpler designs can be achieved.

In FIGS. 6 to 12 an additional and possibly independent embodiment of a syringe 20 is shown, wherein the same reference numerals and component names have been used for the same parts as in the preceding FIGS. 1 to 5. To avoid unnecessary repetition reference is made to the detailed description thereof in the preceding FIGS. 1 to 5.

This further embodiment of the syringe 20 shown here, in particular its syringe head 21, is configured to be similar to that of the syringe head 21 described in relation to FIGS. 1 to 3.

Thus the syringe 20 comprises the syringe barrel 15 for holding the medicine to be delivered, in which the syringe head 21 is arranged at its proximal end and an ejector unit 25 is arranged at its distal end. The syringe head 21 is covered by the protective cap 14 and thus protects the proximal tip of the cannula 3, which projects in the position of rest or starting position, from impurities and prevents unwanted needlestick injuries. The protective cap 14 with its protective cap base 22 is fitted or snapped onto the proximal end of the syringe barrel 15 and preferably mounted thereon by the radial pretensioning of the protective cap base 22 so as to be virtually secure against rotation. By means of holding means in engagement with one another accordingly the protective cap base 22 is also held in axial direction at the proximal end of the syringe barrel 15. Furthermore, between the proximal end of the syringe barrel 15, in particular its end face, and a shoulder of the protective cap base 22 projecting radially in the direction of the longitudinal axis a sealing ring 60 is arranged. In this way a bacteria-tight seal is also obtained in the transitional area between the syringe barrel 15 and the protective cap 14.

In the exemplary embodiment shown here two guide knobs 1 are arranged on the pinion 2 which are arranged in a plane perpendicular to the longitudinal axis and spaced apart from one another in circumferential direction. The latter can be moved for the displacement of the needle unit 12 from the position of rest to the actuation position into engagement with only one of the two slide tracks 10, whereby the activation and the associated axial longitudinal adjustment of the cannula 3 with the cannula holder 4 is performed in the direction of the syringe barrel 15 and in this way the sealing element 7 is pierced in the region of its proximal end by the cannula tip. In this way a line connection is created between the inner chamber of the syringe barrel 15 and the cannula 3. The drive of the pinion 2 is performed by a corresponding rotational movement of the protective cap tip 23 about the longitudinal axis. In this way the web or webs 13 of the pinion 2 are in engagement with the previously described inner lamellae of the protective cap tip 23.

Figure 11:
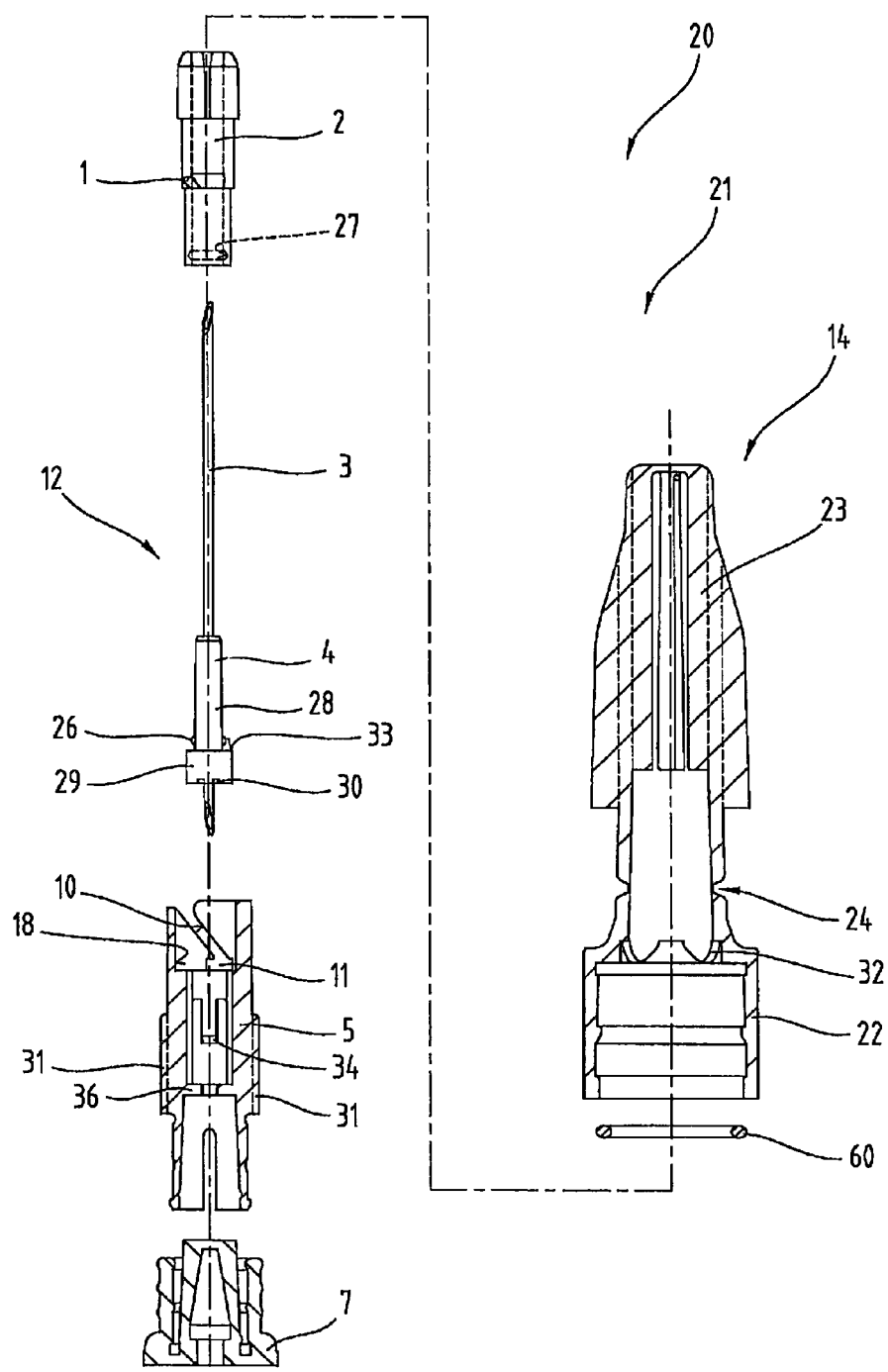
FIG. 11 shows the syringe head and the protective cap according to FIGS. 6 to 9 in an exploded view, in cross-sectional view.
Figure 12:
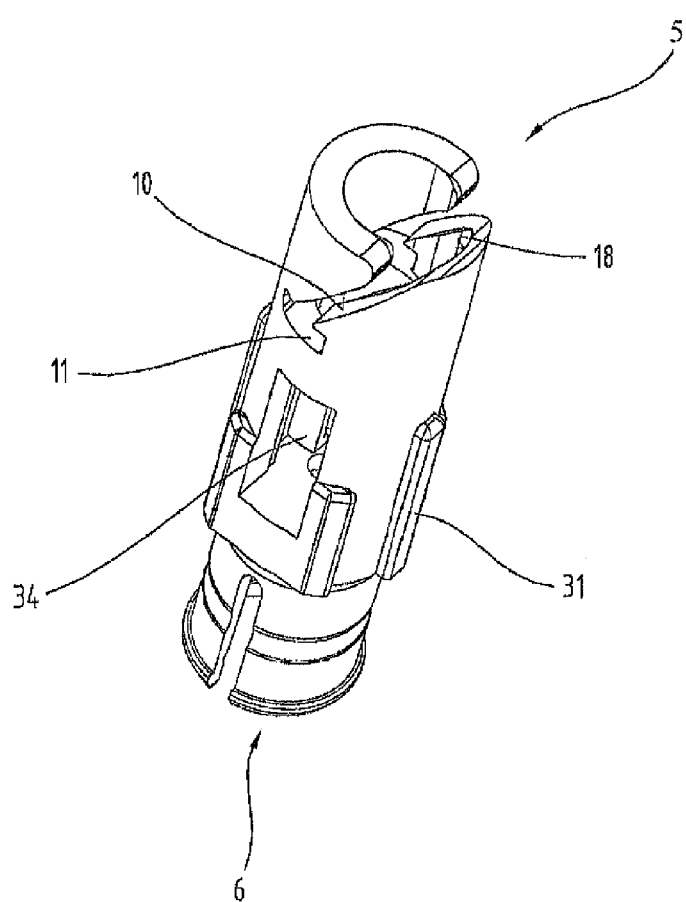
FIG. 12 shows the guide sleeve of the syringe head according to FIGS. 6 to 11, in a schematic view.

As can be seen best from an overview of FIGS. 6, 7 and 11, the area is provided in the region of the proximal end of the guide sleeve 5 which forms the two slide tracks 10. The latter two opposite aligned slide tracks 10 are arranged offset to one another in circumferential direction in order to be moved into engagement with one of the two guide knobs 1 on corresponding activation. To create sufficient freedom of movement for the additional guide knob 1 which is out of engagement with one of the two slide tracks 10, here in a circumferential area between the two slide tracks 10 the free space 18 is formed and is used for holding one of the two guide knobs 1. In the present exemplary embodiment the free space 18 is formed by a radial enlargement and an associated decrease in the wall thickness of the guide sleeve 5. The two slide tracks 10 are thereby in the form of preferably slot-like recesses or openings in the outer wall of the guide sleeve 5 and thus provide even better guiding of one of the two guide knobs 1. At the end of the slide track 10 the previously described preferably horizontal guide extension 11 is formed, in which one of the two guide knobs 1 is arranged after a suitable displacement in the actuation position.

In order to facilitate the assembly process it is an advantage if the needle unit 12, in particular the cannula holder 4, is rotatable with the pinion 2 about the longitudinal axis, but is connected to be locked in axial direction. In addition, as shown best in FIG. 11, at least one radially projecting projection 26 is arranged on the shaft 28 of the cannula holder 4, which can be moved into engagement with a preferably radially peripheral recess 27 in the pinion 2. Preferably, the projection 26 can also be formed to be peripheral which engages in a preferably annular groove, which forms the recess 27, for mutual locking.

Independently of this however it would also be possible to provide the recess 27 in the shaft 28 of the cannula holder 4 and the projection or projections 26 on the pinion 2.

On the shaft 28 of the cannula holder 4 in the region of its distal end a base 29 is formed which projects over the shaft 28 radially. This preferably annular base 29 can be moved with its proximal end at the distal end of the pinion 2 in the locked or held position.

In order to achieve an exact straight axial movement of the cannula 3 during the axial adjustment thereof in the guide sleeve 5, the needle unit 12, in particular the cannula holder 4, needs to guided linearly in the guide sleeve 5. In addition, for example on the base 29 of the cannula holder 4 at least one guiding member 30 is arranged which is in guiding engagement with a guide track not shown in more detail on the inner side of the guide sleeve 5. Preferably, also a plurality of guiding elements 30 are provided with cooperating guiding tracks in the guide sleeve 5. Furthermore, the cannula holder 4 after insertion into the guide sleeve 5 in the position of rest or starting position can be connected in the direction of the proximal side locked in axial direction. In this way also during the assembly process in addition to the longitudinal guiding a specific coupling effect is achieved and an unintentional detachment from the guide sleeve 5 is prevented.

As already described above the protective cap base 22 of the protective cap 14 is snapped onto the proximal end of the syringe barrel 15 and held almost non-rotatably thereon by the radial pretensioning thereof. In order to also prevent a relative displacement of the guide sleeve 5 relative to the protective cap 14, in particular its protective cap base 22, on an outer side of the guide sleeve 5 at least one longitudinal rib 31 is arranged or formed. A section of the guide sleeve 5 is mounted in a through opening of the protective cap base 22, wherein proximal ends of the longitudinal ribs 31 are supported on locking elements 32 provided therefor on the inside of the protective cap 14 mounting the syringe head 21. By means of the interaction of the preferably several longitudinal ribs 31 with the locking element or elements 32 the guide sleeve 5 is held locked relative to the protective cap 14 in its rotation about the longitudinal axis.

In this way, as already described above, the activation of the needle unit 12 can be performed in that the protective cap tip 23 is rotated about the longitudinal axis in one of two directions—clockwise or counterclockwise—and in this way the predetermined breaking point 24 between the protective cap tip 23 and the protective cap base 22 is broken. By means of the drive connection of the protective cap tip 23 with the pinion 2 and then the guided adjustment of the pinion 2 with its guide knob 1 in one of the slide tracks 10 there is an axial displacement of the cannula 3 with the cannula holder 4 in distal direction towards the syringe barrel 15. In this case the cannula holder 4 slides in axial direction guided linearly in the guide sleeve 5 towards the sealing element 7 and pierces the latter.

Once this actuation position has been reached an axial mounting or locking of the needle unit 12 is performed, in particular of the cannula holder 4, on the guide sleeve 5. This is performed in that on the one hand the base 29 of the cannula holder 4 on its proximal side forms a first locking element 33. A further locking element 34 is formed or arranged on the guide sleeve 5 and preferably is arranged on a radially elastically deformable spring arm. The additional locking element 34 grips behind the first locking element 33 in the activation position of the needle unit 12, whereby an axial mounting of the needle unit 12 is achieved in proximal direction. The two locking elements 33, 34 form in the actuation position a locking device 35. The needle unit 12, in particular the base 29, comes to bear in the actuation position on a bottom element 36 arranged on the inside of the guide sleeve 5. In the bottom element 36 a through opening of the passage of the distal end of the cannula 3 is provided. Thus in the actuation position the needle unit 12 is locked on both sides in axial direction with its base 29. One the one hand by means of the bottom element 36 and on the other hand by means of the cooperation of the locking elements 33, 34. By means of the locking element 34 a proximal axial displacement of the cannula holder 4 can be prevented, whereby the delivery of the medicine can be performed by the ejector unit 25 without there being an unwanted release or distancing of the cannula 3 from the syringe 20.

From an overview of FIGS. 6, 8 and 10 the ejector unit 25 is shown in the region of the distal end of the syringe barrel 15, which in turn comprises a plunger 16, a plunger rod 17 and a coupling part 37 coupling or connecting the plunger rod 17 to the plunger 16. The plunger 16 comprises from an end turned towards the plunger rod 17 a blind hole 38 extending into the latter which is closed on the proximal side by a bottom 39. The outside of the plunger 16 bears in a sealing manner, but displaceably by sliding, on the inside of the syringe barrel 15.

The coupling part 37 comprises a base body 40, from which to the plunger 16 a projecting coupling extension 41 extends—i.e. in proximal direction. The coupling extension 41 projects with its coupling extension end 42 into the blind hole 38. In the inactivated starting position of the ejector unit 25 the coupling extension end 42 is preferably arranged spaced apart from the bottom 39 so that the bottom 39 forms a not yet pierced membrane, which closes the inner chamber of the syringe barrel 15 bacteria-tight in cooperation with the plunger 16. Furthermore, in the inactivated starting position the plunger 16 is arranged in axial direction spaced apart from the base body 40. For locking the position of the plunger 16 on the coupling extension 41 at least one first locking element 43 can be arranged or formed on the coupling extension 41, which locking element engages or is inserted in the inactivated starting position into a locking recess 44 arranged in the plunger 16 in the region of the blind hole 38. It would also be possible independently of this to arrange or form the locking element 43 on the plunger 16 and the locking recess 44 on the coupling extension 41.

By means of the interaction of the first locking element 43 with the locking recess 44 an axial mutual mounting or locking of the plunger 16 on the coupling extension 41 is performed. Thus in this position the premounted ejector unit 25 can be inserted into the syringe barrel 15 after filling with the medicine to be administered. Prior to filling with medicine the unit of the syringe head 21 still needs to be mounted or secured onto the syringe barrel 15. In this way firstly the unit of the syringe head 21 can be assembled and pushed in from the distal end into the syringe barrel 15. In this case the unit of the syringe head 21 can be provided ready sterilized. After inserting in sterile conditions the medicine is then inserted. Afterwards the also sterilized ejector unit 25 is also inserted. Thus the inner chamber holding the medicine is sterile until its activation. Only by means of the activation will access be provided to the medicine via the cannula 3.

The coupling extension end 42 of the coupling extension 41 is configured on the side facing away from the plunger rod 17—i.e. at its proximal end—to taper in an arrow-like manner. This arrow-like tapering is provided in order to be able to enter a further blind hole formed in the sealing element 7 and to create between the coupling extension end 42 and the sealing element 7 a coupling connection for the withdrawal movement of the whole unit of the syringe head 21. To form said coupling connection on the coupling extension end 42 preferably at least two locking arms 45 projecting over the cross section of the coupling extension 41 are provided. The locking arm or arms 45 have a specific inherent rigidity and can be pushed by the elastic deformation of the material of the sealing element 7 into the additional blind hole. By means of this configuration of the locking arms 45 the entry of the coupling extension end 42 into the blind hole of the sealing element 7 is possible in a simpler manner and without greater resistance, wherein after the insertion path of the locking arm or arms 45 are arranged behind a shoulder arranged or formed in the blind hole of the sealing element 7. Depending on the strength and selected material of the locking arm 45 the latter can have elastic properties to a certain extent. Because of the small cross section of the locking arm 45 the latter can form the desired coupling connection with the shoulder in the blind hole of the sealing element 7. In this way a specific anchoring or locking of the locking arm or locking arms 45 in the elastically deformable sealing element 7 is achieved during the restoring movement. Particularly with siliconized surfaces of the sealing element 7 this configuration of the locking arms 45 is advantageous instead of a mostly peripheral locking wedge. Thus the shoulder and the through opening arranged in front in distal direction can be designed to have a smaller cross section, which is only used for mounting the cross section of the coupling extension 41. The locking arm or arms 45 projecting over it with the smaller cross-sectional width relative to the entire circumference of the coupling extension 41 then penetrate by means of the elastic deformation of the sealing element 7 and if necessary a radial elastic deformation of the locking arm or arms 45 in connection with a free position in the coupling extension 41 into the blind hole.

To couple the coupling part 37 with the plunger rod 17 on the base body 40 of the coupling part 37 on the side facing the plunger rod 17 elastically deformable coupling arms 46 can be provided which can be coupled detachably to a coupling element 47 formed on the plunger rod 17. In this case the coupling arms 46 are preferably designed to be resilient preferably in radial direction and grip behind the coupling element 47 on the side facing the plunger rod 17. The dimensions of the coupling arms 46 in the coupled position with the coupling element 47 are selected so that the latter have an external dimension which corresponds approximately to the internal dimension of the syringe barrel 15. In this way the disconnection of the plunger rod 17 is not possible until there is specific cross-sectional widening, in order to perform the radial widening of the coupling element 46 and thus perform the disconnection process. As the syringe barrel 15 is mostly made of glass it is an advantage if its inner wall over its entire length has virtually the same cross section or the same cross-sectional dimension.

As shown best from FIG. 8 the ejector unit 25 is in its activated position here in which the coupling extension end 42 has pierced through the bottom 39 of the plunger 16 and with its distal end bears or is supported on the proximal end of the base body 40. In this ejection position the first locking element 43, which was previously arranged in the locking recess 44 of the plunger 16, after the relative displacement bears against the inside of the bottom 39 of the blind hole 38 in the area penetrated by the coupling extension 41. By means of this support effect of the bottom 39 an additional sealing effect is provided on the proximal end side of the plunger in the contact area or through area of the coupling extension 41. This is because the bottom 39 has a relatively thin wall thickness and thus the internal pressure created during the delivery process does not cause any leaking in this area.

FIG. 9 shows the retracted position and thus the safety position of the needle unit 12 inside the syringe barrel 15. In this case the plunger rod 17 has already been separated from the coupling part 37. In order to perform this retraction movement of the plunger 16 more effectively, in addition on the coupling extension 41 between the base body 40 and the first locking element 43 at least one additional locking element 48 can be arranged or formed. The latter lies during the return movement of the ejector unit 25 together with the needle unit 12 on a shoulder 49 formed in the blind hole 38 of the plunger 16. To form the shoulder 39 the blind hole can comprise sections with various different cross sections 50, 51, wherein in the exemplary embodiment shown here the cross section 51 has a smaller cross-sectional dimension than the cross section 50 in the area of the section facing the bottom 39.

As shown best from an overview of FIGS. 9 and 10, as already described, the syringe barrel 15 starting from its narrowed proximal end section towards the distal end has a virtually uniform cross-sectional dimension. At the distal end of the syringe barrel 15 an handling element 52 is also shown in simplified form which is preferably a component of the ejector unit 25. Said handling element 52 is preferably formed by two half bodies which can be joined together in radial direction, which are secured by an extension 53 of the syringe barrel 15 on the latter in axial direction. Any known snapping and/or locking elements can be used for the mutual connection of the two half bodies to form the handling element 52.

To perform the previously described disconnection process between the coupling element 47 of the plunger rod 17 and the coupling arms 46 of the coupling part 37 a clear inner width 54 of a through channel 55 in the handling element 52 in one distal section is greater than an outer cross-sectional dimension of the coupling arms 46 in the unformed position. In this way a radial widening of the coupling arms 46 is made possible in order to perform the uncoupling process.

To achieve the axial securing in position of the coupling part 47 relative to the syringe barrel 15 and thereby avoid the re-use of the syringe 20 it is advantageous if between the coupling part 37, in particular of the base body 40, and the handling element 52 a holding device 56 is formed with interacting holding elements 57, 58. In this exemplary embodiment shown here the first holding element 57 is formed on the base part 40 of the coupling part 37, for example in the form of a peripheral groove-like depression, into which at least the additional holding element 58 engages in the safety position. The additional holding element 58 in the region of the handling element 52 can be configured to be radially resilient or elastically deformable, which after a sufficient restoring movement of the coupling part 37 locks in the first holding element 57 provided therefor. Depending on the configuration and type of selected holding element 57, 58 an axial displacement of the remaining ejector unit 25 and the needle unit 12 can be prevented in at least one direction—proximal and/or distal. Preferably, in this way also a further removal of the remaining ejector unit 25 together with the needle unit 12 can be prevented.

To prevent the re-insertion of the plunger rod 17 with its coupling element 47 into the coupling part 37 in particular its base body 40 with the coupling arms 46, on the handling element 52 in the area of its distal end at least one guide element 59 can be arranged which projects into the cross section of the through channel 55. The guide element 59 can be curved arc-like for example in the direction of the longitudinal axis. Preferably however, a plurality of guide elements 59 are provided in order to prevent the re-insertion of the plunger rod 17 into the syringe 20.

Of course, the represented exemplary embodiments can be modified in various ways within the scope of the concept of the invention, e.g. with respect to the arrangement of the guide knobs 1 relative to one another and/or relative to the locking hook 8, with respect to the materials used and the gradient angle of the slide tracks 10.

The syringe 20 described above is a type of syringe that is already prefilled with medicine and is ready for delivery. This is referred to as a prefilled syringe, in particular a glass single-dose syringe. The material of the syringe barrel 15 is selected to be glass. The inner chamber of the syringe holding the medicine is sealed completely against the inner wall of the syringe barrel 7 in a bacteria-proof manner at its proximal end by the sealing element 7 which is unpierced until activated and at its distal end by the also not yet pierced plunger 16. Only after the activation of the syringe head 21 by rotating the protective cap tip 23 does the distal end of the cannula 3 pierce the bottom of the sealing element 7 and thus forms the line connection to the inner chamber of the syringe barrel 15 and thereby the medicine. Then the stored medicine can be delivered.

In FIGS. 13 to 16 a further and possibly independent embodiment of a syringe 20 is shown, wherein the same reference numerals and components names are used for the same parts as in the preceding FIGS. 1 to 12. To avoid unnecessary repetition reference is made to the detailed description relating to the preceding FIGS. 1 to 12.

The syringe 20 shown here is configured in a similar way as already described in particular with regard to FIGS. 6 to 12. In this embodiment variant it is intended to be possible for the user or operator of such a syringe 20 for the needle to be moved into a safety position after the delivery of the medicine stored in the syringe barrel 15 without any further action by the user. If this occurs without the intervention of the user it is referred to as a passive needle protection system. However, if the user needs to take additional steps after completing the delivery of the medicine from the syringe barrel to ensure that a needle safety position is reached it is referred to as an active needle protection system. This separate step can consist of a deliberate and specific activation of a mechanism.

Therefore, the syringe 20 represented here comprises the syringe barrel 15 for holding the medicine, not shown in more detail, the plunger rod 17 with the connected coupling part 37, on which the plunger 16 can also be arranged. The needle unit 12 is configured such that the latter is covered by the protective cap 14 in the unused position and the distal end of the cannula 3 is still not in flow connection with the inner chamber of the syringe barrel 15. To provide the flow connection the distal end of the cannula 3 needs to be pierced through the sealing element 7, whereby the desired flow connection can be provided. The protective cap 14 can in turn comprise the protective cap base 22 and the protective cap tip 23 connected to the latter in the delivery position. By means of the latter the activation of the cannula 3 is performed as already explained above.

The coupling part 37 is also used here to couple or connect the plunger 16 and the plunger rod 17 to one another. In addition, on the base body 40 of the coupling part 37 on the side turned towards the plunger rod 17 a separate coupling device 61 is provided, wherein the coupling device 61 can comprise cooperating coupling elements 62, 63. The first coupling element 62 shown here can be configured for example as a truncated cone-shaped base which is provided on its side turned towards the base body 40 with an undercut and extends in axial direction. At the proximal end of the plunger rod 17 the additional coupling element or elements 63 are arranged which in the coupling position are in coupling engagement with the first coupling element 62.

Furthermore, at the distal end of the syringe barrel 15 the previously described handling element 52 is arranged through which the plunger rod 17 passes in the center thereof. The handling element 52 is preferably mounted on the extension 53 of the syringe barrel 15.

Figures 15, 16:
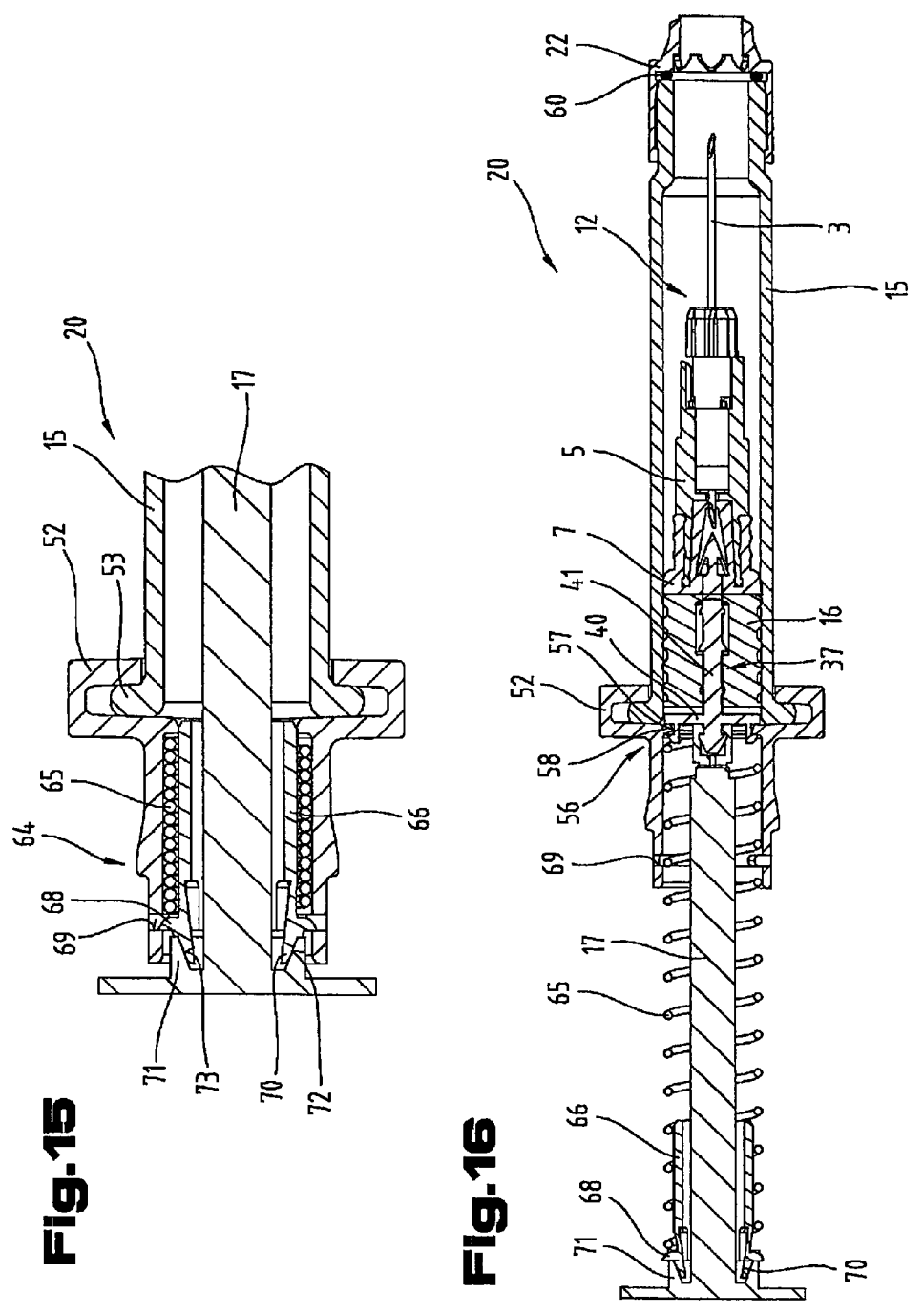

Here between the handling element 52 and the plunger rod 17 a resetting device 64 is provided. In this case "between" means that the resetting device 64 is supported on the one hand on the handling element 52 and on the other hand after its release the plunger rod 17, the coupling part 37, the plunger 16 and the needle unit 12 which can be coupled thereto are displaced in distal direction relative to the syringe barrel 15 from the proximal position to the distal position. This reset position is shown in FIG. 16.

Thus for example the resetting device 64 can comprise at least one spring element 65, which in the pretensioned position or location establishes an adjusting force in axial direction, which is effective after unlocking or releasing the resetting device 64. The spring element 65 can be a compression spring, in particular a helical spring. Thus here the proximal end of the spring element 65 is supported directly on the handling element 52. Furthermore, as viewed in radial direction, between the spring element 65 and the plunger rod 17 a separate, in particular tubular sliding body 66 is arranged. On its outer circumference or around the latter the spring element 65 is arranged. The sliding body 66 is used to support the spring element 65 at its distal end. Furthermore, the sliding body 66 is mounted or supported if necessary detachably in the pretensioned position of the spring element 65 on the handling element 52 in the region of its distal end by means of a retaining device 67.

The retaining device 67 can in turn comprise cooperating retaining elements 68, 69, wherein here for example the retaining element 68 is arranged as a nose-like base on the sliding body 66, which projects over the sliding body 66 in radial direction. The retaining element or elements 68 can be arranged on a released spring arm, whereby the retaining element or elements 68 are pivoted in radial direction in the direction of the longitudinal axis. The additional retaining element 69 cooperating therewith, can for example be a recess, a slot or opening in the handling element 52, on which the first retaining element 68 is supported with the removal of the spring force of the spring element 65.

In this way a pretensioned spring mechanism can be created which on activating or triggering the causes the automatic restoring and thereby the passive needle return.

The syringe 20 is stored prefilled with medicine, as already described above, and is delivered in this way, whereby the activation for the delivery process can be performed as has already been described for FIGS. 1 to 12. In the embodiments according to FIGS. 1 to 12 however it is necessary that by means of active needle resetting the user would have to pull back the needle inside the syringe barrel 15 himself to achieve the protected position.

As best seen from FIG. 15 here a sufficient amount of medicine has already been delivered from the syringe barrel 15, the coupling extension end 42 of the coupling part 37 having been moved into coupling engagement with the sealing element 7 and the thereby coupled needle unit 12.

The release of the retaining device 67 is performed here by cooperating adjusting elements 70, 71. Said adjusting elements 70, 71 should be configured in such a way that after a predefined adjustment movement of the plunger rod 17 relative to the syringe barrel 15 or the handling element 52 arranged thereon the interacting retaining elements 68, 69 of the retaining device 67 are moved so far out of engagement that the pretensioned resetting device 67 exerts a restoring force with its spring element 65, whereby the plunger rod 17 together with the coupled components or elements can be returned so far that at least the needle unit 12 is located with its proximal end of cannula 3 inside the syringe barrel 15 or the protective cap base 22 mounted thereon.

The adjusting elements 70, 71 can have for example adjusting spaces 72, 73 aligned for example conically or at an angle to the longitudinal axis of the syringe 20. By means of the conical alignment or angled inclination of the adjusting spaces 72, 73 the latter—as shown in FIG. 15—can bear against one another, whereby the previously described retaining elements 68, 69 are moved out of locking engagement with one another. The inclined adjusting spaces 72, 73 when lying on top of one another mean that the here nose-like retaining element 68 is displaced in radial direction in the direction of the longitudinal axis and in this way is disconnected from the other retaining element 69. If these two retaining elements 68, 69 are disconnected the spring element 65 of the resetting device 64 by bearing the sliding body 66 on the plunger rod 70 in its distal end can restore the plunger rod 17 together with the components coupled thereto. This protected position of the needle unit 12 is shown in FIG. 16. Thus here for example the first adjusting element 70 is arranged or provided on the sliding body 66 and the additional adjusting element 71 on the plunger rod 17. Thus the release of the retaining elements 68, 69 is performed automatically during the delivery process and no additional separate triggering process needs to be performed.

To avoid the re-activation of the syringe 20 it is possible to provide the previously described holding device 56 with its holding elements 57, 58 between the coupling part 37, in particular its base body 40, and the handling element 52. In this case the holding elements 57, 58 can be formed for example by cooperating locking hooks or locking noses which grip into one another such that in their engagement position the re-activation and thus the displacement of the needle unit 12 relative to the syringe barrel 15 is avoided securely.

In this protected position of the cannula tip of the cannula 3 inside the syringe barrel 15 the whole syringe 20 can be disposed of without any concern.

In this way by means of this configuration of the resetting device 64 the user does not need to perform any additional triggering steps in order to reach the safety position of the cannula 3, but this takes place automatically during the passive needle return by the resetting device 64.

The previously described resetting device 67 can however also be combined with a syringe independently of this, as described for example in WO 2007/112470 A1. Said syringe differs from the present embodiment only in that the cannula from the very beginning is in flow connection with the inner chamber of the syringe barrel and thereby with the medicine. In the embodiment described here in FIGS. 1 to 16 the distal end of the cannula 3 is only brought just before the intended delivery of the medicine in flow connection with the inner chamber of the syringe barrel 15 and thereby with the medicine stored therein.

Furthermore, the unused position of the individual components relative to one another is referred to as the position of rest or original position and the position of the needle unit 12, in which a line connection is produced to the inner chamber of the syringe barrel 15 is referred to as the actuation position. The same operating conditions or positions of the ejector unit 25 can also be defined in these terms. If the needle unit 12 has been returned into the syringe barrel 15, this can be referred to as the disposal or protection position.

Finally, as a point of formality, it should be noted that for a better understanding of the structure of the syringe 20, in particular its syringe head 21 and ejector unit 25, the latter and its components have not been shown to scale in part and have been enlarged and/or reduced in size.

The problem addressed by the independent solutions according to the invention can be taken from the description.

All of the details relating to value ranges in the present description are defined such that the latter include any and all part ranges, e.g. a range of 1 to 10 means that all part ranges, starting from the lower limit of 1 to the upper limit 10 are included, i.e. the whole part range beginning with a lower limit of 1 or above and ending at an upper limit of 10 or less, e.g. 1 to 1.7, or 3.2 to 8.1 or 5.5 to 10.

The exemplary embodiments show possible embodiment variants of the syringe 20, in particular its syringe head 21 and its ejector unit 25, whereby it should be noted at this point that the invention is not restricted to the embodiment variants shown in particular, but rather various different combinations of the individual embodiment variants are also possible and this variability, due to the teaching on technical procedure, lies within the ability of a person skilled in the art in this technical field. Thus all conceivable embodiment variants, which are made possible by combining individual details of the embodiment variants shown and described, are also covered by the scope of protection. Furthermore, also individual features or combinations of features from the various shown and described different exemplary embodiments can represent independent solutions according to the invention.

Mainly the individual embodiments shown in FIGS. 1, 2; 3; 4; 5; 6 to 12; 13 to 16 can form the subject matter of independent solutions according to the invention. The objectives and solutions according to the invention relating thereto can be taken from the detailed descriptions of these figures.

| List of Reference Numbers | |
|---|---|
| 1 | guide knob |
| 2 | pinion |
| 3 | cannula |
| 4 | cannula holder |
| 5 | guide sleeve |
| 6 | coupling |

-continued

| List of Reference Numbers | |
|---|---|
| 7 | sealing element |
| 8 | locking hook |
| 9 | window |
| 10 | slide track |
| 11 | slide extension |
| 12 | needle unit |
| 13 | web |
| 14 | protective cap |
| 15 | syringe barrel |
| 16 | plunger |
| 17 | plunger rod |
| 18 | free space |
| 19 | sealing disc |
| 20 | syringe |
| 21 | syringe head |
| 22 | protective cap base |
| 23 | protective cap tip |
| 24 | predetermined breaking point |
| 25 | ejector unit |
| 26 | projection |
| 27 | recess |
| 28 | shaft |
| 29 | base |
| 30 | guiding element |
| 31 | longitudinal rib |
| 32 | locking element |
| 33 | locking element |
| 34 | locking element |
| 35 | locking device |
| 36 | bottom element |
| 37 | coupling part |
| 38 | blind hole |
| 39 | bottom |
| 40 | base body |
| 41 | coupling extension |
| 42 | coupling extension end |
| 43 | locking element |
| 44 | locking recess |
| 45 | locking arm |
| 46 | coupling arm |
| 47 | coupling element |
| 48 | locking element |
| 49 | shoulder |
| 50 | cross section |
| 51 | cross section |
| 52 | handling element |
| 53 | extension |
| 54 | internal width |
| 55 | through channel |
| 56 | holding device |
| 57 | holding element |
| 58 | holding element |
| 59 | guide element |
| 60 | sealing ring |
| 61 | coupling device |
| 62 | coupling element |
| 63 | coupling element |
| 64 | resetting device |
| 65 | spring element |
| 66 | sliding body |
| 67 | retaining device |
| 68 | retaining element |
| 69 | retaining element |
| 70 | adjusting element |
| 71 | adjusting element |
| 72 | adjusting space |
| 73 | adjusting space |

The invention claimed is:

1. A syringe (20) comprising a syringe barrel (15) for holding a medicine to be administered, an ejector unit (25) arranged at a distal end of the syringe barrel (15), a syringe head (21) arranged at a proximal end of the syringe barrel (15) with a needle unit (12) arranged in a guide sleeve (5) and slidable therein comprising a cannula (3) and a cannula holder (4) and a pinion (2), by means of which the needle unit (12) can be moved axially relative to a syringe barrel (15) from a position of rest to an actuation position and a sealing element (7) arranged at a distal end of the guide sleeve (5) which in the position of rest of the needle unit (12) is unpierced by the cannula (3) and in an activated position of the needle unit (12) is pierced by the cannula (3), wherein the pinion (2) comprises two guide knobs (1), each of which can be moved into engagement optionally with one of two slide tracks (10) provided in the guide sleeve (5), wherein the slide tracks (10) are inclined in opposite directions, and wherein the two guide knobs (1) are arranged spaced apart from one another in a plane aligned perpendicular to a longitudinal axis and in a circumferential direction and in order to displace the needle unit (12) from the position of rest to the actuation position only one of the two guide knobs (1) is moved into engagement with one of the two slide tracks (10).

2. The syringe (20) as claimed in claim 1, wherein in the guide sleeve (5) in a circumferential area between the two slide tracks (10) a free space (18) is formed and the free space (18) is used for mounting the guide knob (1), which during an adjustment of the needle unit (12) is not in engagement with any of the slide tracks (10).

3. The syringe (20) as claimed in claim 1, wherein the cannula holder (4) and the guide sleeve (5) are held in position relative to one another in axial direction in the actuation position by means of cooperating locking elements (33, 34) of a locking device (35).

4. The syringe (20) as claimed in claim 1, wherein the cannula holder (4) is coupled with the pinion (2) to be rotatable about the longitudinal axis but locked in axial direction.

5. The syringe (20) as claimed in claim 1, wherein the cannula holder (4) is mounted linearly in the guide sleeve (5) in axial direction.

6. The syringe (20) as claimed in claim 1, wherein at an end of each slide track (10) a slide extension is provided in which the guide knob (1) can engage in the actuation position of the needle unit (12).

7. The syringe (20) as claimed in claim 1, wherein the distal end of the guide sleeve (5) is configured as a coupling (6).

8. The syringe (20) as claimed in claim 1, wherein on an outer side of the guide sleeve (5) at least one longitudinal rib (31) is arranged, which is supported in a non-rotational manner on a locking element (32) of a protective cap (14) mounting the syringe head (21).

9. The syringe (20) as claimed in claim 1, wherein the ejector unit (25) comprises a plunger rod (17), a coupling part (37) with a base body (40) and a coupling extension (41) projecting to a side facing away from the plunger rod (17) and a plunger (16), wherein the base body (40) of the coupling part (37) is connected detachably to the plunger rod (17) and the plunger (16) comprises a blind hole (38) extending from an end facing the plunger rod (17), which blind hole is closed by a bottom (39), wherein the coupling extension (41) of the coupling part (37) projects into the blind hole (38) and in an inactivated starting position the plunger (16) is arranged spaced apart in axial direction from the base body (40) and also the bottom (39) of the blind hole (38) is not pierced by a coupling extension end (42) of the coupling extension (41), wherein on the coupling extension (41) at least one first locking element (43) is arranged which in the inactivated starting position is inserted into a locking recess (44) formed in the plunger (16) in the area of the blind hole (38).

10. The syringe (20) as claimed in claim 9, wherein the first locking element (43) in an adjoining position of the base body (40) and the plunger (16) rests on the bottom (39) of the blind hole (38) in an area penetrated by the coupling extension (41).

11. The syringe (20) as claimed in claim 9, wherein on the coupling extension (41) between the base body (40) and the first locking element (43) a further locking element (48) is arranged, which during a restoring movement of the ejector unit (25) is supported bearing on a shoulder (49) formed in the blind hole (38) of the plunger (16).

12. The syringe (20) as claimed in claim 9, wherein the coupling extension end (42) is configured to be tapering in an arrow-like manner to the side facing away from the plunger rod (17) and comprises at least one locking arm (45) projecting over a cross section of the coupling extension (41).

13. The syringe (20) as claimed in claim 9, wherein the base body (40) of the coupling part (37) on a side facing the plunger rod (17) comprises elastically deformable coupling arms (46) which are coupled detachably to a coupling element (47) formed on the plunger rod (17).

14. The syringe (20) as claimed in claim 13, wherein the plunger rod also comprises a handling element (52), which can be connected to a distal end of a syringe barrel (15), and an internal width (54) of a through channel (55) in the handling element (52) in a distal section is greater than an outer cross-sectional dimension of the coupling arms (46) in their undeformed position.

15. The syringe (20) as claimed in claim 14, wherein between the base body (40) of the coupling part (37) and the handling element (52) a holding device (56) with interacting holding elements (57, 58) is formed, which when the holding elements (57, 58) are in engagement prevent at least an axial adjustment of the coupling part (37) in proximal direction.

16. The syringe (20) as claimed in claim 14, wherein at least one guiding element (58) is arranged on the handling element (52) in the region of its distal end which projects into the cross section of the through channel (55).

17. The syringe (20) as claimed in claim 9, wherein between the handling element (52) and the plunger rod (17) a resetting device (64) is provided, by means of which the plunger rod (17), the coupling part (37), the plunger (16) and the needle unit (12) connectable therewith can be restored in distal direction relative to the syringe barrel (15).

18. The syringe (20) as claimed in claim 17, wherein the resetting device (64) comprises at least one spring element (65), which is supported at its proximal end on the handling element (52) and at its distal end on a tubular sliding body (66), and the sliding body (66) in a pretensioned position of the spring element (65) can be held releasably on the handling element (52) by means of a retaining device (67).

19. The syringe (20) as claimed in claim 18, wherein release of the retaining device (67) is performed after a predetermined adjustment movement of the plunger rod (17) relative to the syringe barrel (15) by means of interacting adjusting elements (70, 71), wherein at least one first adjusting element (70) is arranged on the sliding body (66) and at least one further adjusting element (71) is arranged on the plunger rod (17).

20. The syringe (20) as claimed in claim 1, wherein a material of the syringe barrel (15) is selected to be glass and an inner chamber of the syringe is filled with medicine and is ready to be administered, wherein the inner chamber of the syringe filled with medicine is sealed completely so as to be bacteria-proof from an inner wall of the syringe barrel (15) at its proximal end by the sealing element (7) which is unpierced until activated and at its distal end by the plunger (16) that is also not yet pierced.

* * * * *